US008121251B2

(12) United States Patent
Raupach et al.

(10) Patent No.: US 8,121,251 B2
(45) Date of Patent: Feb. 21, 2012

(54) METHOD FOR POST-PROCESSING RAW DETECTOR SIGNALS, A COMPUTER PROGRAM PRODUCT, A COMPUTER READIBLE MEDIUM AND A RADIATION DETECTION DEVICE

(75) Inventors: Rainer Raupach, Heroldsbach (DE); Karl Stierstorfer, Erlangen (DE)

(73) Assignee: Siemens Aktiengesellschaft, Munich (DE)

( * ) Notice: Subject to any disclaimer, the term of this patent is extended or adjusted under 35 U.S.C. 154(b) by 587 days.

(21) Appl. No.: 12/292,372

(22) Filed: Nov. 18, 2008

(65) Prior Publication Data

US 2009/0141857 A1 Jun. 4, 2009

(30) Foreign Application Priority Data

Nov. 20, 2007 (DE) .......................... 10 2007 055 387

(51) Int. Cl.
*A61B 6/03* (2006.01)

(52) U.S. Cl. ................................ 378/19; 378/4; 382/131
(58) Field of Classification Search ................ 378/4, 19; 382/128–131; 250/369
See application file for complete search history.

(56) References Cited

U.S. PATENT DOCUMENTS 6,898,263 B2 * 5/2005 Avinash et al. .................... 378/4
2005/0201635 A1 * 9/2005 Mori .............................. 382/274

OTHER PUBLICATIONS

Kachelriess et al., Generalized multi-dimensional adaptive filtering for conventional and spiral single-slice, multi-slice, and cone-beam CT, 2001, Medical Physics, vol. 28, No. 4, pp. 475-490.*
Keselbrener et al., Nonlinear filters applied on computerized axial tomography: Theory and phantom images, 1992, Medical Physics, vol. 19, No. 4, pp. 1057-1064.*

* cited by examiner

*Primary Examiner* — Edward Glick
*Assistant Examiner* — John Corbett
(74) *Attorney, Agent, or Firm* — Harness, Dickey & Pierce, P.L.C.

(57) ABSTRACT

Methods for post-processing raw detector signals of an x-ray or gamma detector are disclosed. According to at least one embodiment of the invention, raw detector signals are filtered, an associated filtered signal is determined at least for a subset of the raw detector signals, and those filtered signals whose signal value is less than zero are then respectively replaced by a signal value greater than zero.

20 Claims, 4 Drawing Sheets

METHOD FOR POST-PROCESSING RAW DETECTOR SIGNALS, A COMPUTER PROGRAM PRODUCT, A COMPUTER READABLE MEDIUM AND A RADIATION DETECTION DEVICE

PRIORITY STATEMENT

The present application hereby claims priority under 35 U.S.C. §119 on German patent application number DE 10 2007 055 387.2 filed Nov. 20, 2007, the entire contents of which is hereby incorporated herein by reference.

FIELD

Embodiments of the invention generally relate to a method for post-processing raw electrical detector signals corresponding to individual pixels of a radiation detector. In particular, they may relate to an x-ray detector or gamma detector, a computer program product having program code for carrying out the method, and/or to a radiation detection device designed to carry out the method.

BACKGROUND

Raw detector signals of individual pixels, for example of a pixel matrix, of a radiation detector usually exhibit pixel noise. Under normal conditions, the pixel noise is determined by the finite number of the radiation quanta striking the radiation detector, and thus by the quantum statistics, and by electronic noise of electronic components. The electronic noise forms a significant component of the pixel noise in the event of high attenuation of the radiation by an object to be examined, that is to say in the event of low average quantum energies of the quanta striking the radiation detector.

By contrast with the quantum noise, which has a Poisson distribution and therefore always leads to raw detector signals with positive signal values, electronic noise can lead to signal values less than zero. Negative signal values lead to image quality problems that are known, for example, by the term "clipping".

Methods for noise reduction and for avoiding clippings are known in which the negative signal values are replaced by physically sensible values, for example by one signal value or by a combination of a number of signal values of adjacent pixels. Attenuation values, also termed projections, are respectively calculated from the signal values postprocessed in this way. In simplified terms, in order to determine the attenuation value the logarithm of the ratio of "unattenuated signal value" to an attenuated, that is to say measured, signal value of the pixel is respectively calculated. The attenuation values are then subjected to noise reducing filtering for the purpose of noise reduction. The filtered attenuation values form the basis for determining an attenuation image which, in the case of x-ray computed tomography, for example, is obtained by a filtered back projection.

A disadvantage in this case is that the attenuation images exhibit corrupted quantitative information. By way of example, this in turn impairs the diagnosis in the case of radiological examinations.

SUMMARY

In at least one embodiment of the invention, a method is provided for post-processing raw electrical detector signals corresponding to individual pixels of a radiation detector, in particular an x-ray detector or gamma detector, in the case of which method corruption of the quantitative information is very largely avoided, it being possible in addition to implement the method in a simple way. A further aim of at least one embodiment is to provide a computer program product suitable for carrying out the method, and a radiation detection device.

A first aspect of at least one embodiment of the invention relates to a method for post-processing raw electrical detector signals corresponding to individual pixels of a radiation detector, in particular an x-ray detector or gamma detector, having the following steps:
  a) providing the raw detector signals,
  b) filtering the raw detector signals, an associated filtered signal being determined at least for a subset of the raw detector signals, and
  c) replacing those filtered signals whose signal value is less than zero by a signal value greater than zero.

The inventors have realized that in the case of the above-described methods according to the prior art a systematic error is induced by virtue of the fact that the replacement of the negative signal values that precedes the filtering causes a displacement of the, in particular quantum statistical, mean value of the respective raw detector signals. Given small signal strengths of the raw detector signals, this leads, in turn, to systematic overestimations of the signals, and thus to systematic errors. The systematic errors lead to a corruption of the quantitative information content that is propagated into the attenuation images.

In accordance with at least one embodiment of the inventive method, the raw detector signals are filtered before the replacement of negative signal values of the raw detector signals, an associated filtered signal being respectively determined at least for a subset of the raw detector signals. The quantum statistical mean value of the signal values of the raw detector signals of the relevant pixels is maintained. At the same time, the component of negative signal values is drastically reduced.

The comparatively few negative signal values remaining after filtering are respectively replaced by positive signal values after the filtering. Since the number of the negative signal values is substantially reduced, the systematic errors can be substantially reduced by comparison with the methods according to the prior art. This is propagated in the attenuation images, which consequently exhibit a higher quantitative information content.

After the filtering and replacement of the negative signal values there is thus a data record that forms an optimum basis for determining the attenuation images. In order to determine the attenuation images it is possible to use the filtered signals, or the replaced filtered signals, which are also denoted as filtered signals in the scope of at least one embodiment of this invention, to determine logarithmic attenuation values. Such attenuation values are also known by the designations of logarithmic projection values or line integrals. In the case of computed tomography examinations, the attenuation values form the basis for reconstructing a two- or three-dimensional attenuation image.

Within the scope of at least one embodiment of the invention, a negative signal value is replaced by a value greater than zero. It is also admittedly possible in principle to replace a negative signal value by zero. However, this would mean in physical terms that the x-ray or gamma radiation is absorbed 100%, and this is unlikely with real radiation detection systems. To this extent, replacement by a value greater than zero, constitutes a physically sensible replacement for concrete applications. Furthermore, replacement by zero would be problematic for the calculation of the attenuation values, since this is generally accomplished by taking the logarithm of the ratio of unattenuated to measured signal strength.

In the case of at least one embodiment of the inventive method, it is possible to improve the contrast-to-noise or the strength-to-noise ratio as against conventional methods further in the event of strongly absorbing examination objects for example with thick patients in the case of x-ray computed tomography. The reason for this is that in the event of strong absorption of the radiation the electronic noise is a significant component of the total noise, and so substantially more raw detector data with negative signal values occur in the event of strong absorption.

Within the meaning of at least one embodiment of the invention, the raw detector signals denote direct electronic output signals of the respective pixels of the detector, which are also denoted as pixels or detector elements. This means, in particular, that no, in particular noise reducing, filtering or mathematical operation such as, for example, taking of logarithms, has yet been applied to the raw detector signals before step b). Digitization, rebinning or resorting of the raw detector data do not fall under the term of mathematical operation here.

The filtering in step b) can be, for example, filtering with a noise reducing filter core. In particular, the filtering can comprise a convolution of the raw detector signals with the aid of a convolution core with low pass effect.

In the case of a radiation detector, the pixels can be arranged in two dimensions, in a row direction and a channel direction. In this case, a tensor of the second stage can be used as convolution core. The tensor can have the following form:

$$\kappa = \frac{1}{\eta}(a_{i,j}),$$

where it holds that:
$a_{i,j} \in \mathrm{IR}$, that is to say the $a_{i,j}$ are real numbers,
$i,j \in \mathrm{IN}$, that is to say i,j are natural numbers,
$\eta$ is the sum of all $a_{i,j}$: $\eta = \Sigma a_{i,j}$, and
i, j or j, i are smaller than a respective number of the pixels of the detector in row or column direction.

The filtering can be carried out easily and quickly with the aid of such a tensor. One example may be a binomial or Gaussian filter. A simple example of this is given, for example, by:

$$\kappa = \frac{1}{16}\begin{pmatrix} 1 & 2 & 1 \\ 2 & 4 & 2 \\ 1 & 2 & 1 \end{pmatrix}$$

assuming at least three rows and three channels, which is usual in the case of x-ray computer tomographs of recent generation.

In step c) of at least one embodiment of the inventive method, a filtered signal less than zero can be replaced on the basis of at least one further filtered signal with a signal value of greater than or equal to zero. It is thereby possible to simulate the actual circumstances particularly accurately, thus facilitating obtaining the quantitative information content. During the replacement, at least one further filtered signal of an adjacent—preferably in channel direction—pixel can be used, and this can be implemented particularly easily.

The filtering can, furthermore, be carried out in time direction, that is to say the direction of consecutive projections, or in a combination of filtering in time, row and column directions. In this case, it is possible to use as convolution core a tensor of the third stage that can have the following form:

$$\kappa' = \frac{1}{\eta'}(b_{i,j,k}).$$

It holds here that:
$b_{i,j,k} \in \mathrm{IR}$, that is to say the $b_{i,j,k}$ are real numbers,
$i,j,k \in \mathrm{IN}$, that is to say i,j,k are natural numbers,
$\eta'$ is the sum of all $b_{i,j,k}$: $\eta' = \Sigma b_{i,j,k}$, and
i, j, k, are smaller than a respective number of the pixels of the detector in row and column directions, or smaller than the number of the recorded projections.

The tensor can be built up, however, by a tensor product composed of one dimensional low pass filters, for example with Gaussian characteristics, $$\kappa'_{i,j,k} = \frac{1}{4^3}\left[\begin{pmatrix} 1 \\ 2 \\ 1 \end{pmatrix}_i \otimes \begin{pmatrix} 1 \\ 2 \\ 1 \end{pmatrix}_j \otimes \begin{pmatrix} 1 \\ 2 \\ 1 \end{pmatrix}_k\right].$$

According to one refinement of at least one embodiment of the method, the filtering is embedded in an adaptive filtering method. The term "adaptive" is intended here to mean that at least one subset of the raw detector signals is filtered as a function of the signal strength thereof and/or the signal strength of prefiltered signals derived from the raw detector signals. It is thereby possible to take account of conditions in the raw detector signals that are local with reference to channel and row directions. The loss of quantitative information and also of image sharpness, for example, can be reduced to a minimum in this case.

In the case of the adaptive filtering method, prefiltered signals can be determined for at least one subset of the raw detector signals, the filtered signals being obtained by mixing the prefiltered signals with the raw detector signals. The prefiltered signals can be obtained from the raw detector signals, for example by filtering with the aid of a noise reducing filter core or any other desired filter core.

Mixing weights used in the mixing can be determined from the respective raw detector signals and/or prefiltered signals, it being possible, in particular, to determine an individual mixing weight for each raw detector signal and/or prefiltered signal taken into account in the mixing. To this end, it is possible that the mixing weights decrease in accordance with a respectively prescribed function for increasing signal values of the prefiltered signals and increase for decreasing signal values of the prefiltered signals. In particular, it is possible that the mixing weights approximate zero for increasing signal values of the prefiltered signals, and approximate unity for decreasing signal values of the prefiltered signals.

The mixing can be calculated in accordance with the following rule for a pixel with the respectively assigned raw detector signal and prefiltered signal:

$\tilde{S} = (1-w)\cdot S + w\cdot S^F$, in which $\tilde{S}$ denotes the result of the mixing, that is to say the filtered signal,
w denotes the respective mixing weight,
S denotes the raw detector signal of the pixel, and
$S^F$ denotes the prefiltered signal of the pixel.
The weight for S results from the condition that the mixing of S and $S^F$ must be normalized, and thereby has the value 1−w.

Mixing in accordance with the preceding rule can be carried out with particular ease and particularly effectively with regard to the computing time to be estimated for a computer unit for carrying out at least one embodiment of the inventive method.

By way of example, in this case the mixing weight w can be a function of the signal value of the raw detector signals, and be unity for signal values of the raw detector signals less than or equal to a first bound, be zero for signal values greater than or equal to a second bound, and fall continuously from unity to zero for signal values between the first and second bounds. The continuous fall can be a linear fall. The function describing the mixing weight w has the form of a falling ramp in this case.

A second aspect of at least one embodiment of the invention relates to a computer program product comprising program code whose execution on a computer unit effects at least one embodiment of the inventive method.

A third aspect of at least one embodiment of the invention relates to a radiation detection device, in particular an x-ray computer tomograph, comprising a computer unit designed to carry out at least one embodiment of the inventive method.

Reference may be made to the statements relating to at least one embodiment of the inventive method, which are valid analogously, because of advantages and advantageous effects of the computer program product and of the radiation detection device.

BRIEF DESCRIPTION OF THE DRAWINGS

Example embodiments of the invention are explained in more detail below. In the drawings.

DETAILED DESCRIPTION OF THE EXAMPLE EMBODIMENTS

Various example embodiments will now be described more fully with reference to the accompanying drawings in which only some example embodiments are shown. Specific structural and functional details disclosed herein are merely representative for purposes of describing example embodiments. The present invention, however, may be embodied in many alternate forms and should not be construed as limited to only the example embodiments set forth herein.

Accordingly, while example embodiments of the invention are capable of various modifications and alternative forms, embodiments thereof are shown by way of example in the drawings and will herein be described in detail. It should be understood, however, that there is no intent to limit example embodiments of the present invention to the particular forms disclosed. On the contrary, example embodiments are to cover all modifications, equivalents, and alternatives falling within the scope of the invention. Like numbers refer to like elements throughout the description of the figures.

It will be understood that, although the terms first, second, etc. may be used herein to describe various elements, these elements should not be limited by these terms. These terms are only used to distinguish one element from another. For example, a first element could be termed a second element, and, similarly, a second element could be termed a first element, without departing from the scope of example embodiments of the present invention. As used herein, the term "and/or," includes any and all combinations of one or more of the associated listed items.

It will be understood that when an element is referred to as being "connected," or "coupled," to another element, it can be directly connected or coupled to the other element or intervening elements may be present. In contrast, when an element is referred to as being "directly connected," or "directly coupled," to another element, there are no intervening elements present. Other words used to describe the relationship between elements should be interpreted in a like fashion (e.g., "between," versus "directly between," "adjacent," versus "directly adjacent," etc.).

The terminology used herein is for the purpose of describing particular embodiments only and is not intended to be limiting of example embodiments of the invention. As used herein, the singular forms "a," "an," and "the," are intended to include the plural forms as well, unless the context clearly indicates otherwise. As used herein, the terms "and/or" and "at least one of" include any and all combinations of one or more of the associated listed items. It will be further understood that the terms "comprises," "comprising," "includes," and/or "including," when used herein, specify the presence of stated features, integers, steps, operations, elements, and/or components, but do not preclude the presence or addition of one or more other features, integers, steps, operations, elements, components, and/or groups thereof.

It should also be noted that in some alternative implementations, the functions/acts noted may occur out of the order noted in the figures. For example, two figures shown in succession may in fact be executed substantially concurrently or may sometimes be executed in the reverse order, depending upon the functionality/acts involved.

Spatially relative terms, such as "beneath", "below", "lower", "above", "upper", and the like, may be used herein for ease of description to describe one element or feature's relationship to another element(s) or feature(s) as illustrated in the figures. It will be understood that the spatially relative terms are intended to encompass different orientations of the device in use or operation in addition to the orientation depicted in the figures. For example, if the device in the figures is turned over, elements described as "below" or "beneath" other elements or features would then be oriented "above" the other elements or features. Thus, term such as "below" can encompass both an orientation of above and below. The device may be otherwise oriented (rotated 90 degrees or at other orientations) and the spatially relative descriptors used herein are interpreted accordingly.

Although the terms first, second, etc. may be used herein to describe various elements, components, regions, layers and/or sections, it should be understood that these elements, components, regions, layers and/or sections should not be limited by these terms. These terms are used only to distinguish one element, component, region, layer, or section from another region, layer, or section. Thus, a first element, component, region, layer, or section discussed below could be termed a second element, component, region, layer, or section without departing from the teachings of the present invention.

Identical or functionally identical elements are denoted throughout by the same reference symbols in the figures. The x-ray computer tomograph is considered in detail below only to the extent required for understanding embodiments of the invention.

Figure 1:
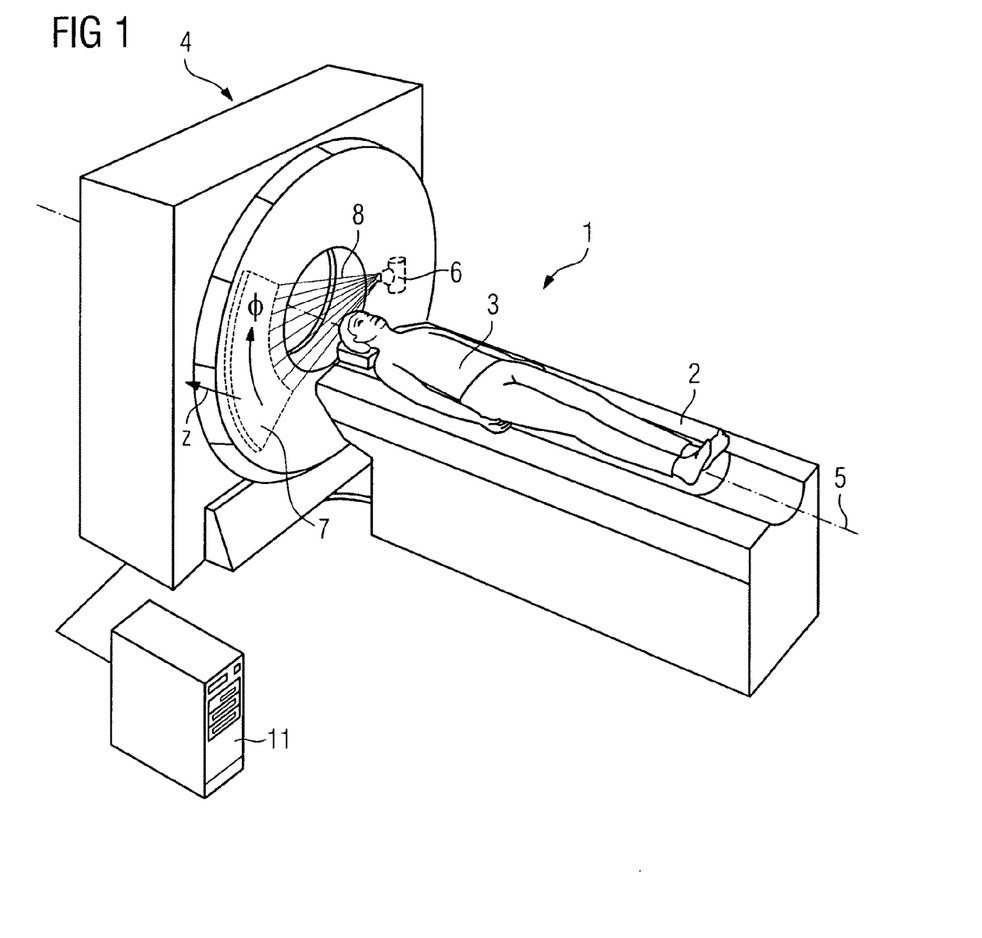
FIG. 1 shows an x-ray computer tomograph having a computer unit for carrying out an embodiment of the inventive method.

FIG. 1 shows an x-ray computer tomograph 1 having a patient's support table 2 with a patient 3 present thereon for examination. The x-ray computer tomograph 1 has a gantry 4 in whose housing there is accommodated an x-ray detector system supported in a fashion capable of rotating about a system axis 5. The x-ray detector system comprises an x-ray tube 6 and an x-ray detector 7 arranged lying opposite thereto. During an examination of the patient 3, for example a scanning of a subregion of the patient's body, x-radiation 8 emanates from the x-ray tube 6 in the direction of the x-ray detector 7. The x-radiation 8 is attenuated by passage through the patient's body. The component of the x-radiation 8 not absorbed by the patient's body is detected by means of the x-ray detector 7. A computer unit 11 is provided to postprocess electrical signals generated by means of the x-ray detector.

The x-ray detector 7 has detector elements that are arranged in two dimensions in a row direction z and a channel direction Φ and are also denoted as detector pixels and form the pixel matrix in their entirety. In what follows, the detector pixels are indicated by i in the row direction, and the number of the detector pixels in the channel direction Φ is indicated by j. The detector pixels supply electrical signals that behave linearly in relation to the incident x-radiation 8 over wide ranges. Within the scope of embodiments of this invention, these electrical signals form the raw detector signals that are denoted by $S_{i,j}$.

An embodiment of the inventive method is applied to the raw detector signals. No intermediate mathematical operation in the sense described further above takes place.

Figure 2:
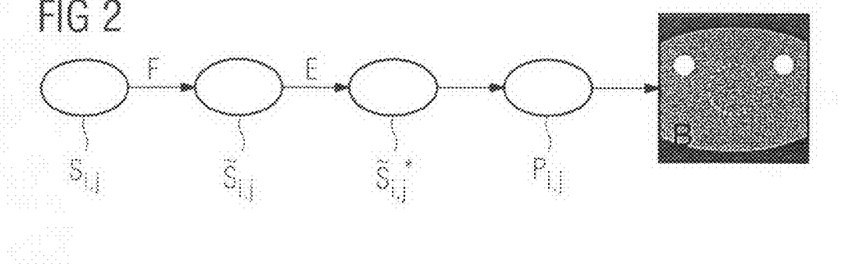
FIG. 2 shows a schematic flow chart of an embodiment of the inventive method.

A schematic flow chart of an embodiment of the inventive method is shown in FIG. 2. The raw detector signals $S_{i,j}$ are firstly subjected to a noise reducing filtering F. It is also possible to subject only a subset of the raw detector data $S_{i,j}$ to the filtering. Filtered signals $\tilde{S}_{i,j}$ obtained by filtering are analogously indicated by i and j, respectively.

The raw detector signals $S_{i,j}$ have a noise component. The noise component comprises quantum noise, which is conditioned by the finite number of the quanta of the x-radiation 8 and is subjected to a Poisson distribution, and electronic noise, which is caused by electronic components and the like. To this end, FIG. 3 displays a diagram illustrating the principle of the profile of the ratio of total noise to quantum noise, with reference to a water phantom for an assumed typical, constant tube current I of the x-ray tube 6. In the diagram, the ratio of total noise to quantum noise is plotted in cm in ordinate direction against the thickness D, measured in the beam path of the x-radiation, of the water phantom. Taking account of the fact that the total noise is essentially composed of quantum noise and electronic noise, it results indirectly that the electronic noise increases strongly in the range from 25 cm thickness D of the water phantom. The reason for this is that the x-radiation 8 is increasingly more strongly absorbed with increasing thickness D, and so the intensity of the x-radiation striking the x-ray detector 7 decreases strongly. The component of the electronic noise substantially independent of the radiation intensity increases correspondingly.

Figure 3:
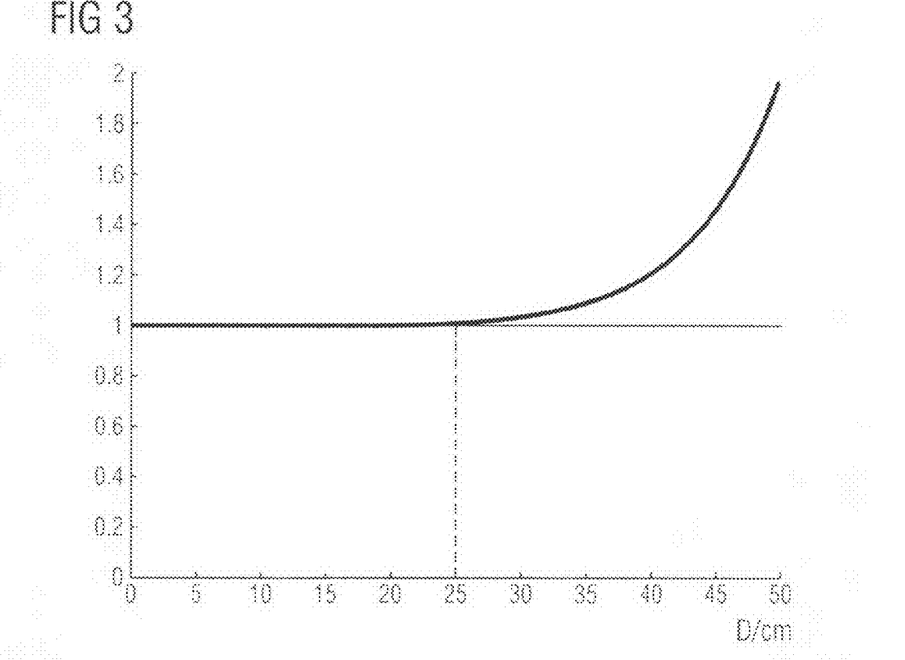
FIG. 3 shows a diagram illustrating the ratio of total noise to quantum noise.

The influence of the electronic noise may be further explained using the following example. A typical computed tomography system is used as the basis, a water phantom with a thickness D of 40 cm, a tube voltage of 120 kV, a tube current I of 150 mA in conjunction with a measurement period of 0.33 s, integration time of 107 μs, and 0.6 mm beam collimation being used. The reconstruction of the CT images is done with the aid of a filtered back projection and a typical convolution core for soft part display in the human body. Assuming the quantum noise with a Poisson distribution and a variance $\sigma^2$ proportional to the respective raw detector signal $S_{i,j}$, a noise value σ=183 HU (Hounsfield Units) results for the quantum noise in the attenuation image in the center of the water phantom. If electronic noise is taken into account in addition, on the one hand there is an increase in the noise value to σ=730 HU, which represents an increase of approximately 300%, and on the other hand raw detector signals $S_{i,j}$ with negative signal values occur in about 1% of the channels.

Owing to the inventive filtering of the raw detector signals $S_{i,j}$, the component of the negative signal values in the filtered signals $\tilde{S}_{i,j}$ can be reduced to 0.0002%, it being possible to avoid a change in the quantum statistical mean values.

The few remaining negative signal values are replaced by positive signal values after the filtering in a replacement step E. Signal values $\tilde{S}_{i,j}*$ obtained after the replacement are likewise denoted as filtered signals. The attenuation values or projection values $P_{i,j}$ for reconstructing a tomographic attenuation image B are calculated from the filtered signals $\tilde{S}_{i,j}*$ obtained after replacement.

An embodiment of the inventive method can be used to reduce the noise value from σ=730 HU in the center of the water phantom to σ=214 HU. The latter is only approximately 17% above the value for pure quantum noise. Moreover, systematic errors that are caused by negative signal values and lead to a reduction in the quantitative information content in the attenuation image B can be drastically reduced.

The preceding example is based on a filtering of the raw detector signals $S_{i,j}$ with the aid of a Gaussian filter $$\kappa = \frac{1}{16}\begin{pmatrix} 1 & 2 & 1 \\ 2 & 4 & 2 \\ 1 & 2 & 1 \end{pmatrix}.$$

Filtering is in no way restricted to this type of filter here.

At least one adjacent further filtered signal $\tilde{S}_{i,j}$ with physically sensible signal values can be used—with reference to the pixels—to replace the negative signal values of the filtered signals $\tilde{S}_{i,j}$. Physically sensible means in this case that only signal values greater than zero are used, for example.

Figure 4:
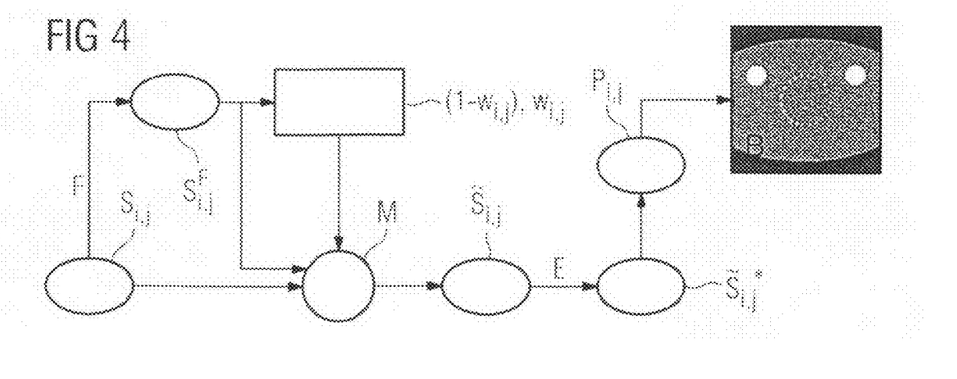
FIG. 4 shows a schematic flow chart of a refinement of an embodiment of the inventive method.

FIG. 4 shows a schematic flow chart of a refinement of an embodiment of the inventive method. In the refinement, the filtering of the raw detector signals $S_{i,j}$ is designed as an adaptive filtering method. This means that the filtering is carried out as a function of local circumstances of the image matrix.

The starting point is, in turn, the raw detector signals $S_{i,j}$. The raw detector signals $S_{i,j}$ are subjected to a filtering F. Prefiltered signals $S_{i,j}^F$ respectively corresponding to the raw detector signals $S_{i,j}$ are obtained from the filtering. The prefiltered signals $S_{i,j}^F$ can be determined from the raw detector signals $S_{i,j}$, for example by filtering with the filter core κ specified above. Any other desired filter cores than that proposed are also possible.

Likewise conceivable is a filtering in time direction, or a combination of a filtering in time, row and column directions, for example with the convolution core κ' specified above.

After being determined, the prefiltered signals $S_{i,j}^F$ are mixed with the raw detector signals $S_{i,j}$. In this case, mixing weights $w_{i,j}$ used for the mixing M are determined for the raw detector signals $S_{i,j}$ or the prefiltered signals $S_{i,j}^F$ are determined on the basis of the prefiltered signals $S_{i,j}^F$. It is also conceivable to use the raw detector signals $S_{i,j}$ in addition or exclusively in order to determine the mixing weights $w_{i,j}$.

The mixing M of the raw detector signals $S_{i,j}$ and the prefiltered signals $S_{i,j}^F$ can be performed in accordance with the following rule:

$$\tilde{S}_{i,j} = (1-w_{i,j}) \cdot S_{i,j} + w_{i,j} \cdot S_{i,j}^F,$$

with the respective filtered signals $\tilde{S}_{i,j}$ being obtained as a result of the mixing M.

If negative signal values occur in the filtered signals $\tilde{S}_{i,j}$ thus obtained, they are replaced in a similar way as described above.

A function dependent on the prefiltered signals $S_{i,j}^F$ can be used to determine the mixing weights $w_{i,j}$. For example, the following falling ramp function can be used for the mixing weights $w_{i,j}$:

$$w_{i,j} = \begin{cases} 1 & \text{if} \quad S_{i,j}^F \leq S_a \\ \dfrac{S_b - S_{i,j}^F}{S_b - S_a} & \text{if} \quad S_a < S_{i,j}^F < S_b \\ 0 & \text{if} \quad S_b \leq S_{i,j}^F, \end{cases}$$

In this case, $S_a$ denotes a first bound, and $S_b > S_a$ a second bound. Qualitatively, this ramp function fulfils the property that the mixing weights $w_{i,j}$ of the prefiltered signals $S_{i,j}^F$ tend toward unity for small signal strengths and zero for large signal strengths. Such a tendential profile is sensible because the problem of negative signal values occurs precisely with small signal strengths of the raw detector signals $S_{i,j}$, and the noise component is higher than with large signal strengths. Apart from the above ramp function, it is also possible to conceive any other desired functions that preferably have the abovementioned property.

Figure 5:
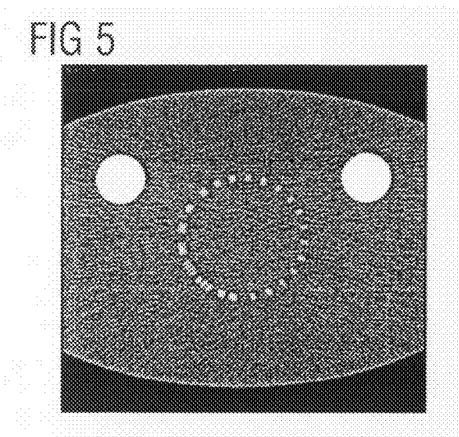
FIG. 5 to FIG. 7 show attenuation images, based on simulations, for illustrating the advantageous effects of embodiments of the inventive method.
Figure 6:
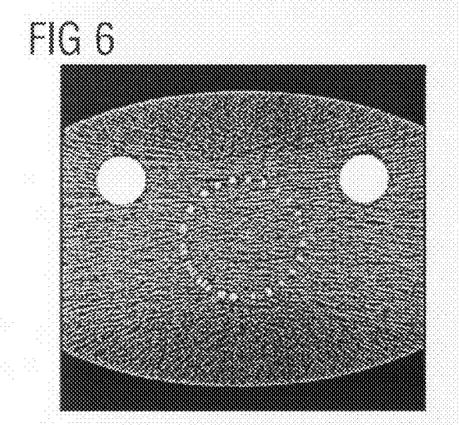
Figure 7:
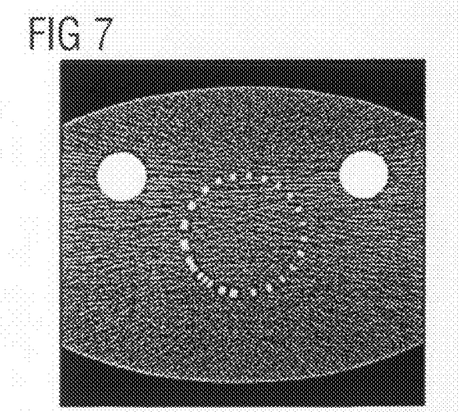

Attenuation images based on simulations are shown in FIG. 5 to FIG. 7 in order to explain the advantageous effects of an embodiment of the inventive method. With the exception of FIG. 5, use is made in the simulation of boundary conditions that correspond to those of a real x-ray computed tomography system, an elliptical phantom 9 approximately the shape of the human body and having a number of objects with higher absorption coefficients than that of the base material (water) 10 serving as examination object. The attenuation images are simulated two dimensional, tomographic reconstruction images, the same layer or cutting plane being illustrated in each case.

FIG. 5 differs from FIG. 6 and FIG. 7 to the extent that only quantum noise and no electronic noise is contained in the raw detector signals on which the simulated reconstruction is based. By contrast, electronic noise is contained in the raw detector signals on which FIG. 6 and FIG. 7 are based.

Horizontally running stripe artifacts are visible in the attenuation image of FIG. 5. These stripe artifacts are caused by the inhomogeneities 10 and elliptic shape of the phantom 9. These stripe artifacts are not caused by simulation, but also occur in real attenuation images, for example of the human body.

FIG. 6 shows an attenuation image analogous to FIG. 5 that has been determined using the customary method according to the prior art. It is evident that the stripe artifacts are more clearly expressed by a multiple.

Like FIG. 6, FIG. 7 shows an analogous attenuation image like FIG. 5. The attenuation image of FIG. 7 has been determined by applying an embodiment of the inventive method. It is clearly to be seen that stripe artifacts are clearly less expressed by comparison with the attenuation image of FIG. 6. The attenuation image of FIG. 7 determined by using an embodiment of the inventive method may clearly be seen to have a higher quantitative information content than that of FIG. 6. This means, in turn, that the diagnostic value of the attenuation image of FIG. 7 is greater than that of FIG. 6.

Figure 8:
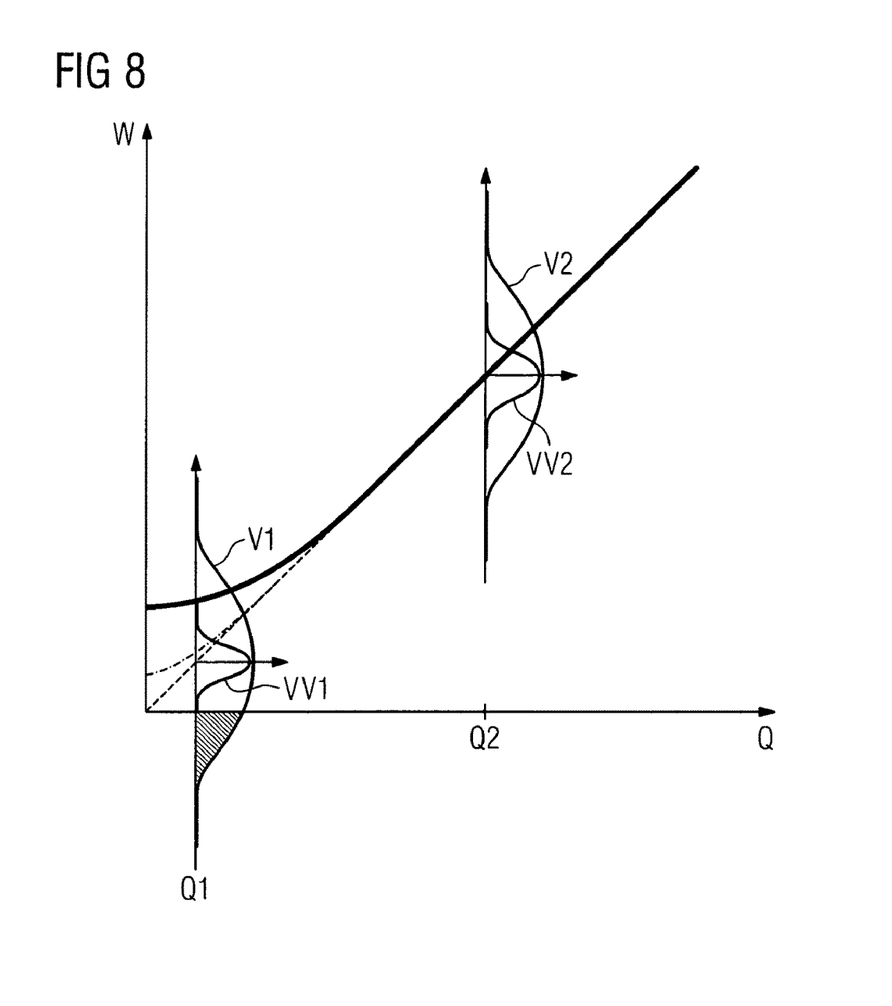
FIG. 8 shows a diagram illustrating systematic errors in the case of the method according to the prior art.

FIG. 8 shows a diagram for illustrating systematic errors in the case of a method according to the prior art. The diagram illustrates the dependence of the signal values W of the raw detector signals $S_{i,j}$ on the quantum energies Q of the x-radiation 8. In the ideal case, illustrated by a dashed straight line, the signal values W are the raw detector signals $S_{i,j}$ depend linearly on the quantum energies Q. Electronic noise, which always occurs in real systems, causes a statistical softening of the ideal profile, something which is illustrated for two selected quantum energies Q1 and Q2 by distribution functions $V_1$ and $V_2$. Negative signal values W can occur in the case of low quantum energies Q, as in the case of the quantum energy Q1, for example, and this is illustrated by the hatched part of the distribution function $V_1$.

If, as in the case of the method according to the prior art, the negative signal values W are now replaced, owing to the relatively broad distribution function $V_1$ this leads to a systematic signal overestimation in a relatively wide range of low quantum energies Q. This is made clear in FIG. 8 from the bent solid line.

By contrast, if, as in the case of an embodiment of the inventive method, a filtering of the raw detector signals $S_{i,j}$—which are essentially linearly dependent on the quantum energies Q—is carried out before the replacement of the negative signal values, the distribution functions $V_1$ and $V_2$ can be scaled down by a multiple. The distribution functions according to the inventive filtering are denoted by $VV_1$ and $VV_2$. Consequently, negative signal values do not occur until there are much lower quantum energies Q, and so the region of systematic signal overestimation can be substantially reduced. The latter is illustrated by the dashed and dotted line in FIG. 8 and has the consequence that the quantitative information content in the attenuation images is much greater by comparison with conventional methods.

In summary, it is clear that the quantitative information content of the attenuation images can be held at a high level by the inventive method. This contributes to the fact that more accurate diagnoses can be made on the basis of the attenuation images.

Further, elements and/or features of different example embodiments may be combined with each other and/or substituted for each other within the scope of this disclosure and appended claims.

Still further, any one of the above-described and other example features of the present invention may be embodied in the form of an apparatus, method, system, computer program and computer program product. For example, of the aforementioned methods may be embodied in the form of a system or device, including, but not limited to, any of the structure for performing the methodology illustrated in the drawings.

Even further, any of the aforementioned methods may be embodied in the form of a program. The program may be stored on a computer readable media and is adapted to perform any one of the aforementioned methods when run on a computer device (a device including a processor). Thus, the storage medium or computer readable medium, is adapted to store information and is adapted to interact with a data processing facility or computer device to perform the method of any of the above mentioned embodiments.

The storage medium may be a built-in medium installed inside a computer device main body or a removable medium arranged so that it can be separated from the computer device main body. Examples of the built-in medium include, but are not limited to, rewriteable non-volatile memories, such as ROMs and flash memories, and hard disks. Examples of the removable medium include, but are not limited to, optical storage media such as CD-ROMs and DVDs; magneto-optical storage media, such as MOs; magnetism storage media, including but not limited to floppy disks (trademark), cassette tapes, and removable hard disks; media with a built-in rewriteable non-volatile memory, including but not limited to memory cards; and media with a built-in ROM, including but not limited to ROM cassettes; etc. Furthermore, various information regarding stored images, for example, property information, may be stored in any other form, or it may be provided in other ways.

Example embodiments being thus described, it will be obvious that the same may be varied in many ways. Such variations are not to be regarded as a departure from the spirit and scope of the present invention, and all such modifications as would be obvious to one skilled in the art are intended to be included within the scope of the following claims.

What is claimed is:

1. A method for post-processing raw electrical detector signals corresponding to individual pixels of a radiation detector, comprising:
   providing the raw detector signals corresponding to individual pixels of the radiation detector;
   filtering the raw detector signals, an associated filtered signal being determined at least for a subset of the raw detector signals, for each raw detector signal in the subset, the filtering is embedded in adaptive filtering, the adaptive filtering including,
      determining prefiltered signals for at least one subset of the raw detector signals, the determining including filtering the raw detector signals, and
      obtaining the filtered signals by mixing the prefiltered signals with the raw detector signals; and
   replacing each of the filtered signals whose signal value is less than zero, by a value greater than zero.

2. The method as claimed in claim 1, wherein the filtering comprises a convolution of the raw detector signals with the aid of a convolution core with low pass effect, the convolution core being a tensor of a second or third stage.

3. The method as claimed in claim 1, further comprising:
   determining logarithmic attenuation values to determine an attenuation image.

4. The method as claimed in claim 1, wherein
   the filtering includes a convolution of the raw detector signals with the aid of a convolution core with low pass effect, and
   the pixels are arranged in two dimensions, in a row direction and a channel direction, and the convolution core ($\kappa$) is a tensor of a second stage of form $$\kappa = \frac{1}{\eta}(a_{i,j}),$$

where:
   $a \in \mathbb{R}$, $i,j \in \mathbb{IN}$, $\eta = \Sigma a_{i,j}$, in which
   i, j or j, i are smaller than a number of pixels in row or column direction.

5. The method as claimed in claim 4, wherein the tensor ($\kappa$) has the following form:

$$\kappa = \frac{1}{16}\begin{pmatrix} 1 & 2 & 1 \\ 2 & 4 & 2 \\ 1 & 2 & 1 \end{pmatrix}.$$

6. The method as claimed in claim 4, wherein the filtering is carried out in at least one of a time direction, and in a combination of the filtering in time, row and column directions.

7. The method as claimed in claim 6, wherein use is made as convolution core of a tensor of the third stage that has the following form:

$$\kappa' = \frac{1}{\eta'}(b_{i,j,k}),$$

in which case it holds here that:
   $b_{i,j,k} \in \mathbb{R}$, $i,j,k \in \mathbb{IN}$, $\eta'$ is the sum of all $b_{i,j,k}$: $\eta' = \Sigma b_{i,j,k}$, and i, j, k are smaller than a respective number of the pixels of the detector in row and column directions, or smaller than the number of the recorded projections.

8. The method as claimed in claim 1, wherein the replacement of a filtered signal of less than zero in the replacing is performed on the basis of at least one further filtered signal with a signal value greater than zero.

9. The method as claimed in claim 8, wherein the pixel corresponding to the further filtered signal is adjacent to the pixel of the filtered signal to be replaced.

10. The method as claimed in claim 1, wherein mixing weights used for the mixing are determined from at least one of the respective raw detector signals and the prefiltered signals.

11. The method as claimed in claim 10, wherein the mixing weights decrease in accordance with a respectively prescribed function for increasing signal values of the prefiltered signals, and increase for decreasing signal values of the prefiltered signals.

12. The method as claimed in claim 11, wherein the mixing weights approximate zero for increasing signal values of the prefiltered signals, and approximate unity for decreasing signal values of the prefiltered signals.

13. The method as claimed in claim 1, wherein the mixing of the raw detector signals and prefiltered signals assigned to the same pixel is carried out in accordance with the following rule:

$$\tilde{S} = (1-w) \cdot S + w \cdot S^F, \text{ in which}$$

$\tilde{S}$ denotes the filtered signal as mixing value for the respective pixel,
   w denotes the respective mixing weight,
   S denotes the raw detector signal of the pixel, and
   $S^F$ denotes the prefiltered signal of the pixel.

14. The method as claimed in claim 13, wherein the mixing weight w is a function of the signal value of the raw detector signals ($S_{i,j}$), and is unity for signal values of the raw detector signals ($S_{i,j}$) less than or equal to a first bound ($S_a$), is zero for signal values greater than or equal to a second bound ($S_b$), and falls continuously from zero to unity for signal values between the first ($S_a$) and second bounds ($S_b$).

15. The method as claimed in claim 14, wherein the mixing weight (w) falls linearly between the first ($S_a$) and second bounds ($S_b$).

16. A non-transitory computer program product comprising program code whose execution on a computer unit is configured to effect a method as claimed in claim 1.

17. The method as claimed in claim 1, wherein the method is for post-processing raw electrical detector signals corresponding to individual pixels of at least one of an x-ray detector and a gamma detector.

18. The method as claimed in claim 17, further comprising:

determining logarithmic attenuation values in order to determine a tomographic attenuation image.

19. A non-transitory computer readable medium including program segments for, when executed on a computer device, configured to cause the computer device to implement the method of claim 1.

20. A radiation detection device, comprising:

means for providing the raw detector signals;

means for filtering the raw detector signals, an associated filtered signal being determined at least for a subset of the raw detector signals, for each raw detector signal in the subset, the filtering is embedded in adaptive filtering, the adaptive filtering including, determining prefiltered signals for at least one subset of the raw detector signals, the determining including filtering the raw detector signals, and obtaining the filtered signals by mixing the prefiltered signals with the raw detector signals; and means for replacing each of the filtered signals whose signal value is less than zero, by a value greater than zero.

\* \* \* \* \*